US00PP34942P2

(12) United States Plant Patent
Van Swieten

(10) Patent No.: US PP34,942 P2
(45) Date of Patent: Jan. 24, 2023

(54) ***PHALAENOPSIS* ORCHID PLANT NAMED 'PHA441188'**

(50) Latin Name: ***Phalaenopsis* hybrid**
Varietal Denomination: PHA441188

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,546

(22) Filed: Aug. 19, 2022

(51) Int. Cl.
*A01H 6/62* (2018.01)
*A01H 5/02* (2018.01)

(52) U.S. Cl.
USPC ..... Plt./360

(58) Field of Classification Search
USPC ..... Plt./360
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHA441188', particularly characterized by having purplish-pink striped flowers with reddish-purple lips, flowers that are flat in lateral view, and whiskers that are reddish-purple and striped with white tips, is disclosed.

3 Drawing Sheets

Genus and species: *Phalaenopsis* hybrid.
Variety denomination: 'PHA441188'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA441188'.

The new *Phalaenopsis* plant is a product of a planned breeding program conducted by the inventor in Bleiswijk, the Netherlands. The objective of this breeding program was to create a new *Phalaenopsis* plant with attractive purplish-pink striped flowers with reddish-purple lips suitable for potted plant production.

The new *Phalaenopsis* plant 'PHA441188' is a result of cross-pollination made by the inventor in June 2014 in Bleiswijk, the Netherlands, of the proprietary female, or seed parent, *Phalaenopsis* hybrid 'PHALLOEL' (EU Certificate No. EU21604), with a proprietary male, or pollen parent, *Phalaenopsis* hybrid '40427-04' (unpatented).

The new *Phalaenopsis* was selected by the inventor as a single plant within the progeny of the stated cross-pollination in a controlled greenhouse in Bleiswijk, the Netherlands, in April 2017. Asexual reproduction of the new *Phalaenopsis* plant by meristem tissue culture since 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 14, 2021 (Application No. 2021/2255), by Applicant who obtained the subject matter disclosed directly from the inventor. 'PHA441188' has not been made publicly available or sold anywhere in the world prior to the effective filing date of this application with the exception of sales or disclosures made one year or less before the effective filing date of this claimed invention by Applicant who obtained 'PHA441188' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA441188' as a new and distinct variety of *Phalaenopsis* plant:

1) Purplish-pink striped flowers with reddish-purple lips;
2) Flower shape in lateral view is flat; and
3) Whiskers are reddish-purple and striped with white tips.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2022. Colors in the photographs may differ from the color values cited in the detailed botanical description, which accurately describe the actual colors of the new variety.

DESCRIPTION OF THE NEW VARIETY

Figure 1:
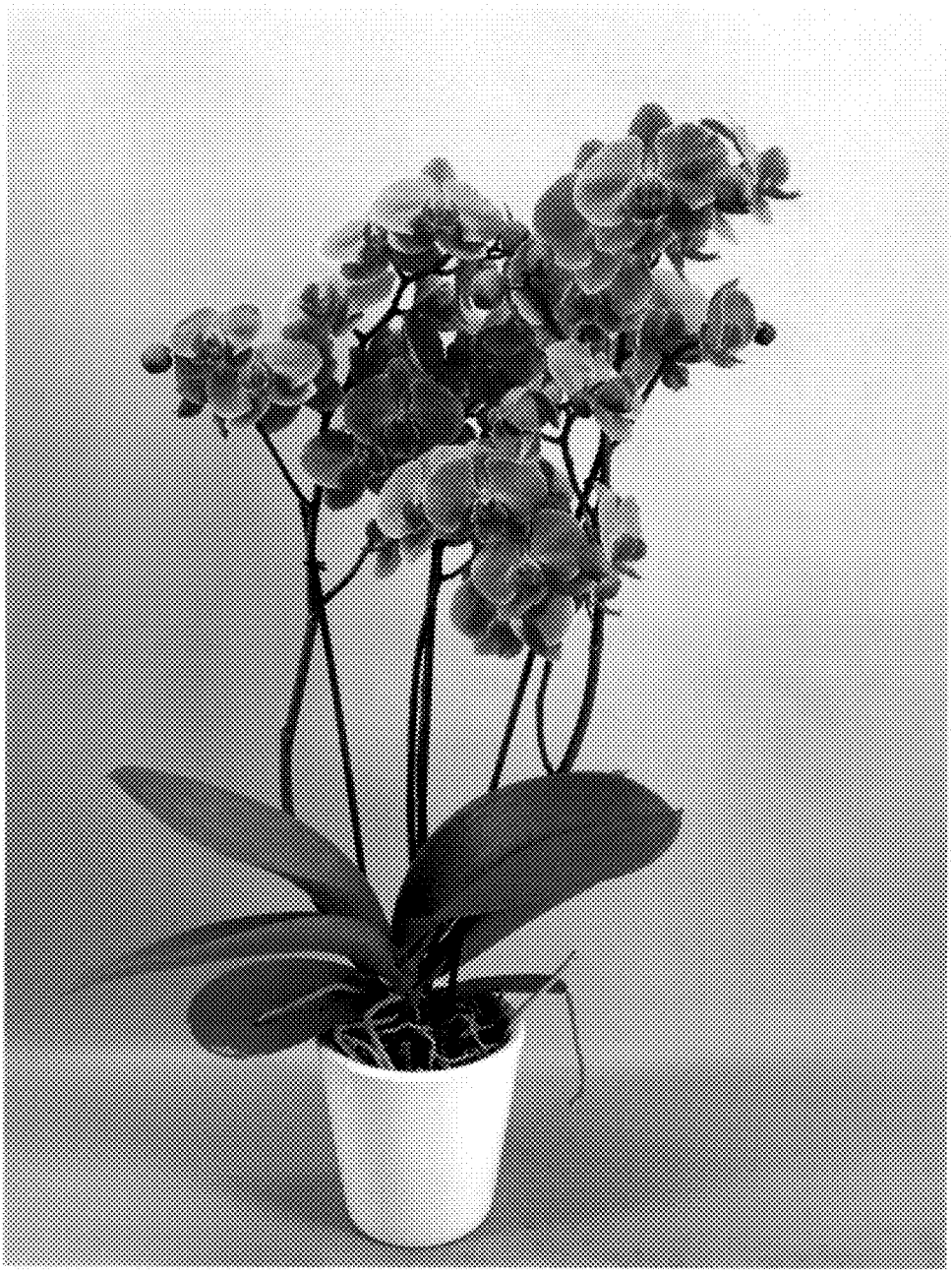
FIG. 1 shows the overall plant habit, including blooms, buds, and foliage of 'PHA441188'.
Figure 2:
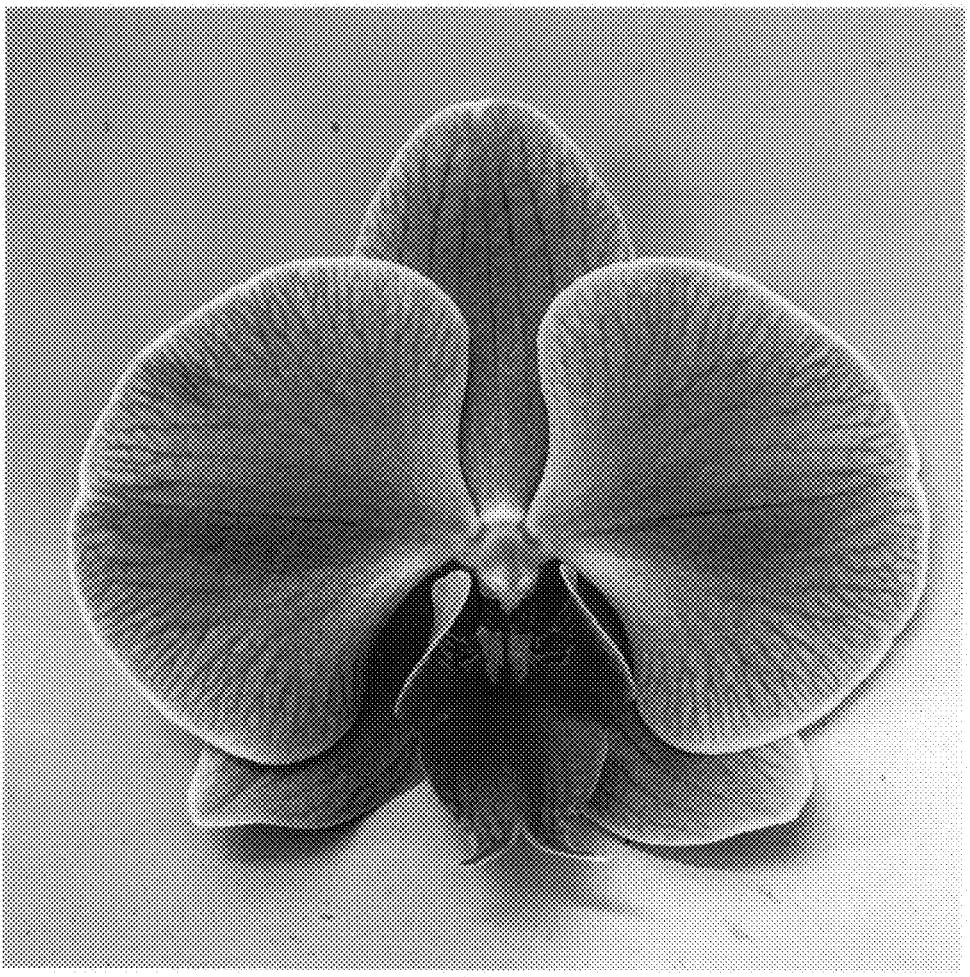
FIG. 2 shows a close-up of a flower of 'PHA441188'.
Figure 3:
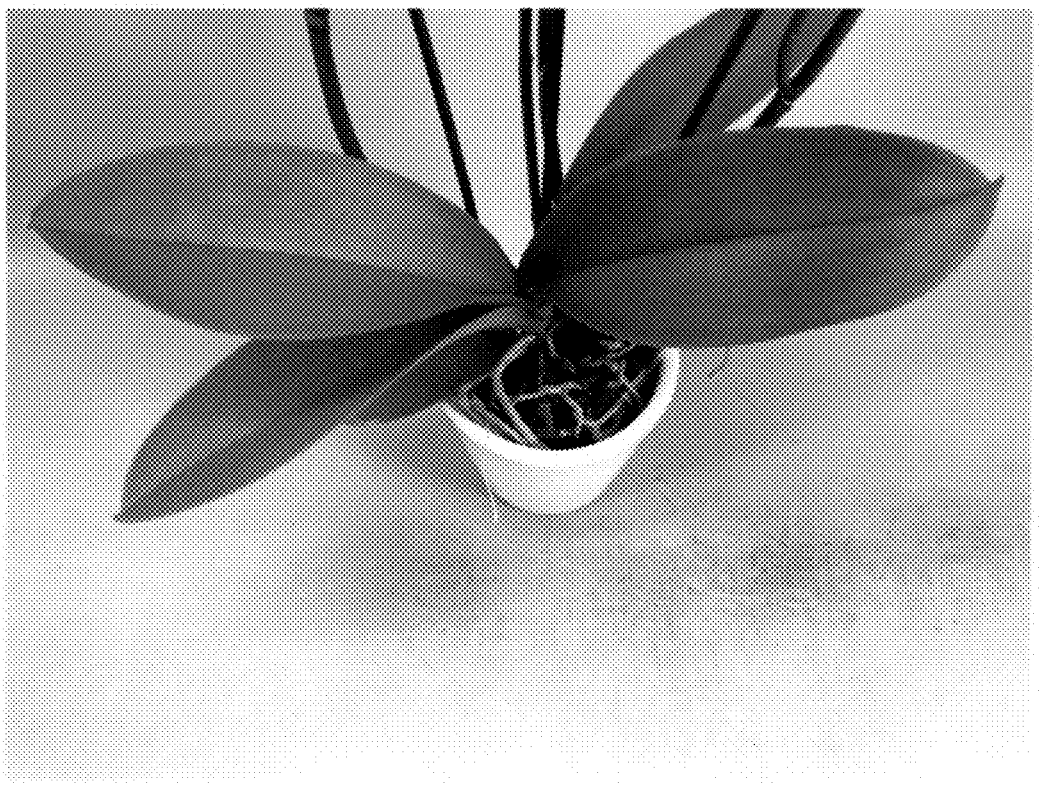
FIG. 3 shows a close-up, overhead view of the leaves of 'PHA441188'.

The following detailed description sets forth the distinctive characteristics of 'PHA441188'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were detelinined under 4000-6000 lux natural light in a greenhouse in Bleiswijk, the Netherlands. Observations and measurements were made in April 2022 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHA441188'.

Parentage:

*Female parent.*—*Phalaenopsis* cultivar 'PHALLOEL'.

*Male parent.*—*Phalaenopsis* cultivar '40427-04' (unpatented).

Propagation:

*Type.*—Meristem tissue culture.

Roots:

*Root description.*—Greyed-green (a color in between RHS 190B and RHS 190C) colored roots with branching lateral roots having yellow-green (RHS N144D) with a touch of purplish-red (RHS N77B) colored root tips.

Plant:

*Crop time to flowering.*—Following asexual propagation (in vitro), the rooted cuttings grow for 20-24 weeks. After transplantation into 12-cm pots, the plants are finished after 48 to 50 weeks.

*Growth habit of the peduncle.*—Upright to slightly pendent with panicle inflorescence.

*Height* (*from soil level to top of inflorescence*).—Approximately 56.0 cm to 61.0 cm.

*Width* (*measured from leaf tips*).—About 38.0 cm to 40.0 cm.

*Vigor.*—Strong.

Leaves:

*Mature leaves.*—Quantity per plant: 8 to 9 leaves are produced before flowering. Length (fully expanded): 22.0 cm to 24.0 cm. Width: 8.5 cm to 9.5 cm. Position of the broadest part of the leaf: At the middle. Shape: Oblong. Base shape: Moderately elongated. Apex: Obtuse, slightly asymmetric. Leaf blade angle with the petiole (measured from the horizontal position): Between 25 degrees and 40 degrees. Leaf margin: Entire. Color: Upper surface: RHS 146B. Lower surface: RHS 146C. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146C.

Peduncle:

*Quantity per plant.*—2 to 4.

*Number of flowers per peduncle.*—15 to 20.

*Length.*—56.0 cm to 61.0 cm.

*Diameter.*—7.0 mm to 8.0 mm.

*Strength.*—Strong.

*Aspect.*—Upright to slightly pendent.

*Texture.*—Smooth.

*Color.*—Mix of brown (RHS 200B) and yellow-green (RHS 146C).

*Internode length.*—2.0 cm to 3.0 cm.

Inflorescence description:

*Appearance.*—Upright to slightly pendent, panicle inflorescence with bilaterally symmetrical flowers that open in succession beginning with the lowermost flower.

*Number of inflorescences.*—2 to 4.

*Inflorescence size.*—Height (from base to tip): 300.0 mm to 400.0 mm.

*Flowering time.*—First flowers can be expected 10 to 11 months after planting in a 12-cm pot.

*Flower.*—Height: 80.0 mm to 85.0 mm. Diameter: 90.0 mm to 95.0 mm. Depth of lip: 21.0 mm to 23.0 mm.

*Flower shape.*—Flat.

*Flower longevity.*—On the plant: 9 to 11 weeks.

*Fragrance.*—Absent.

*Flower bud.*—Average size: Large. Length: 23.0 mm to 25.0 mm. Width: 20.0 mm to 22.0 mm. Shape: Egg shaped. Color: Reddish-purple (RHS N79D) with dark purplish-red shade (RHS N79C).

*Petals.*—Arrangement: Open/free. Shape: Semi-circular. Apex: Emarginated asymmetric. Margin: Moderately undulated. Length (from base to tip): 42.0 mm to 44.0 mm. Width: 54.0 mm to 56.0 mm. Position of the broadest part of the petal: Toward the base. Color (when fully opened): Upper surface: Basic color: Purplish-pink (RHS N78C). Over color: Reddish-purple (RHS N78B) shade and stripes. Lower surface: Basic color: Light reddish-purple (RHS N78D). Over color: Purplish-pink (RHS N78C) shade and stripes. Number of spots, dots, and stripes on the petals (upper surface): Many stripes. Color of spots, dots, and stripes on the petals (upper surface): RHS N78B. Density of netting of the petals (upper surface): None. Color of the netting (upper surface): None.

*Dorsal sepal.*—Shape: Elliptic. Apex: Emarginated symmetric. Margin: Entire. Length (from base to tip): 45.0 mm to 47.0 mm. Width: 32.0 mm to 34.0 mm. Position of the broadest part of the dorsal sepals: Toward the base. Color (when fully opened): Upper surface: Basic color: Purplish-pink (RHS N78C). Over color: Reddish-purple (RHS N78B) shade, stripes, and netting. Lower surface: Basic color: Light reddish-purple (RHS N78D). Over color: Reddish-purple (RHS N78B) shade and netting. Number of spots, dots, and stripes on the dorsal sepals (upper surface): Medium stripes. Color of spots, dots, and stripes on the dorsal sepals (upper surface): RHS N78B. Density of netting of the dorsal sepals (upper surface): Low. Color of the netting: RHS N78B.

*Lateral sepals.*—Shape: Ovate. Apex: Obtuse asymmetric. Margin: Entire. Length (from base to tip): 45.0 mm to 47.0 mm. Width: 27.0 mm to 29.0 mm.

Position of the broadest part of the lateral sepals: Toward the base. Color (when fully opened): Upper surface: Basic color: Purplish-pink (RHS N78C). Over color: Hint of light yellow-green (RHS 145D) with very small dots (RHS 72A) at the base; stripes (RHS N78B); shaded (RHS N78B). Lower surface: Basic color: Purplish-pink (RHS N78C). Over color: Reddish-purple shade (RHS N78B); reddish-purple (RHS N78A) midvein. Number of spots, dots, and stripes on the lateral sepals (upper surface): Medium dots and medium stripes. Color of spots, dots, and stripes on the lateral sepals (upper surface): Dots (RHS 72A) and stripes (RHS N78B). Density of netting of the lateral sepals (upper surface): None. Color of the netting (upper surface): Not applicable.

*Labellum* (*lip*).—Whiskers: Present. Length of whiskers: 8.0 mm to 10.0 mm. Color of whiskers: Reddish-purple (RHS N78B), striped (RHS N78B) with white (RHS NN155C) tips. Pubescence on the lip: Absent.

*Lateral lobe.*—Shape: Type IV (as described in the International Union for the Protection of New Varieties of Plants (UPOV) Test Guidelines for *Phalaenopsis*); weakly spatulate Margin: Undulated (widely wavy). Length: 22.0 mm to 24.0 mm. Width: 14.0 mm to 16.0 mm. Color: Upper surface: Hint of white (RHS NN155A) with purplish-red (RHS 59B) stripes; purplish-pink (RHS N78C) with reddish-purple (RHS N78A) stripes toward, the margin. Lower surface: White (RHS NN155B) on one side at the base; purplish-pink (RHS N78C) with reddish-purple (RHS N78B) stripes on one side toward the margin. Number of spots and stripes on the lateral lobe: Few stripes. Color of spots and stripes on the lateral lobe: RHS 59B. Density of netting of the lateral lobe: None. Color of the netting: None.

*Apical lobe.*—Shape: Rhombic. Margin: Entire. Length: 20.0 mm to 22.0 mm. Width: 21.0 mm to 23.0 mm. Color: Upper surface: Reddish-purple (RHS N78B); reddish-purple (RHS N78A) shade, stripes, and netting toward margins. Lower surface: Reddish-purple (RHS N78C); purplish-red (RHS 72A) at the middle from base. Number of spots and stripes on the apical lobe: Few to medium. Color of spots and stripes on the apical lobe: RHS N78A. Density of netting of the apical lobe: Low. Color of the netting: RHS N78A. Bump and ridge (upper and lower surface): Not present.

*Callus.*—Average size: Medium to large. Height: 8.0 mm to 9.0 mm. Length: 5.0 mm to 6.0 mm. Width: 5.0 mm to 6.0 mm. Color: Yellow (RHS 7A), spotted (RHS 59B); reddish-purple (RHS N78A) front and toward sides.

Reproductive organs:

*Column.*—Length: 9.0 mm to 11.0 mm. Diameter: 5.0 mm to 6.0 mm. Color: Purplish-pink (RHS N78C) at the base with reddish-purple (RHS N78B) tips.

*Pollinia.*—Quantity: 2. Diameter: 0.8 mm to 1.0 mm. Color: Orange (RHS 24A).

*Ovary.*—Length: 9.0 mm to 11.0 mm. Diameter: 2.5 mm to 2.8 mm.

*Pedicel.*—Length: 35.0 mm to 37.0 mm. Diameter: 2.9 mm to 3.2 mm. Color: Hint of yelloW-green (RHS 146C) with purplish-red (RHS N77B) overcolor at the base; light yellow-green (RHS 195C) with purplish-pink shade (RHS N78C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA441188' differs from the female parent plant, cultivar 'PHALLOEL' (EU Certificate No. EU21604), in that 'PHA441188' has rhombic apical lobes and emarginated dorsal sepal apexes, whereas 'PHALLOEL' has ovate apical lobes and obtuse dorsal sepal apexes. Additionally, 'PHA441188' has a striped and shaded flower pattern, whereas 'PHALLOEL' has a striped flower pattern.

'PHA441188' differs from the male parent plant, cultivar '40427-04' (unpatented), in that 'PHA441188' has rhombic apical lobes, whereas '40427-04' has triangular apical lobes. 'PHA441188' has a dotted callus pattern and striped, shaded flower pattern, whereas '40427-04' has a flecked callus pattern and dotted, flecked, and edged flower pattern.

'PHA441188' is most similar to the commercial *Phalaenopsis* plants named 'PHALFEWYP' (U.S. Plant Pat. No. 31,514) and 'PHAGUIQDI' (U.S. Plant Pat. No. 32,207). 'PHA441188' differs from the commercial variety 'PHALFEWYP' in that 'PHA441188' has rhombic apical lobes and striped pattern of apical lobes, whereas 'PHALFEWYP' has triangular apical lobes and an even pattern of apical lobes. Additionally, 'PHA441188' has a smaller flower diameter and whiskers that are reddish-purple with white tips, whereas 'PHALFEWYP' has whiskers that are purplish-red.

'PHA441188' differs from the commercial variety 'PHAGUIQDI' in that 'PHA441188' has weakly spatulated lateral lobes, whereas 'PHAGUIQDI' has spatulated lateral lobes. Additionally, 'PHA441188' has a wider leaves and shorter whiskers than 'PHAGUIQDI'.

I claim:

1. A new and distinct variety of *Phalaenopsis* plant named 'PHA441188', substantially as described and illustrated herein.

* * * * *